United States Patent [19]
Berndt

[11] Patent Number: 5,814,474
[45] Date of Patent: Sep. 29, 1998

[54] DIRECT IDENTIFICATION OF MICROORGANISMS IN CULTURE BOTTLES

[75] Inventor: Klaus W. Berndt, Stewartstown, Pa.

[73] Assignee: Becton Dickinson and Company, Franklin Lakes, N.J.

[21] Appl. No.: 685,255

[22] Filed: Jul. 23, 1996

[51] Int. Cl.[6] .................................................. C12Q 1/04
[52] U.S. Cl. ........................ 435/34; 435/30; 435/287.5
[58] Field of Search ........................... 435/30, 34, 287.5, 435/287.4, 288.1, 288.4, 300.1, 303.1, 304.1, 807, 809

[56] References Cited

U.S. PATENT DOCUMENTS

| | | | |
|---|---|---|---|
| 4,073,691 | 2/1978 | Ahnell et al. | 435/287.5 |
| 4,887,455 | 12/1989 | Payne et al. | 73/27 R |
| 4,971,900 | 11/1990 | Ahnell et al. | 435/287.5 |

FOREIGN PATENT DOCUMENTS

| | | | |
|---|---|---|---|
| 2-240565 | 9/1990 | Japan | 435/287.5 |
| 95/33848 | 12/1995 | WIPO . | |

*Primary Examiner*—William H. Beisner
*Attorney, Agent, or Firm*—Alan W. Fiedler

[57] ABSTRACT

The present invention discloses a method for identifying microorganisms, directly in culture bottles, after they have become positive. The identification is accomplished within a time span of one to three hours. No liquid has to be removed from any of the culture bottles, which reduces the danger of accidents significantly. The invention can be applied to specimens such as for example, blood, urine or sputum.

8 Claims, 4 Drawing Sheets

DIRECT IDENTIFICATION OF MICROORGANISMS IN CULTURE BOTTLES

FIELD OF THE INVENTION

The present invention relates to a method for identifying microorganisms in culture bottles, after they have become positive. This identification can be accomplished in a brief time span, of, for example, one to three hours. As an example, the invention can be applied to identify bacteria in a specimen such as blood or urine, or to identify mycobacteria in specimen such as sputum or blood.

BACKGROUND OF THE INVENTION

Usually, the presence of biologically active agents, such as bacteria in a patient's blood, can be determined by the use of culture bottles. A typical quantity of 1 to 10 ml of blood is injected through a rubber septum which encloses the culture bottle, into the sterile culture bottle containing a culture medium. The vial is incubated at 37° C. and monitored for bacterial growth.

Known instrumental methods detect changes in the carbon dioxide content of the culture bottles, which is a metabolic by-product of bacterial growth. Recently, automated blood culture systems have been developed which involve disposing a chemical sensor inside the vial. These sensors respond to changes in the carbon dioxide concentration by changing their color or by changing their fluorescence intensity (see, e.g., Thorpe et al., "BacT/Alert: An Automated Colorimetric Microbial Detection System",. J. Clin. Microbiol., Jul. 1990, pp. 1608–12; U.S. Pat. No. 4,945,060; and Fraatz, R. et al. "Detection of Biological Activities in a Specimen by Measuring a Fluorescent Signal of a Substance to Indicate the Presence of Microorganisms, ", EP 448923, Oct. 1991).

As a matter of experience, approximately 10% of all incubated blood culture bottles will exhibit bacterial growth. After detecting the presence of bacteria, it is important to identify the organisms. As an example, *Staphylococcus aureus* and *Streptococcus pneumoniae*, when found in a blood culture are usually representative of significant clinical disease. In contrast, non-*S. aureus* species of Staphylococcus, in particular *S. epidermidis*, although potentially of clinical importance, are usually found to be merely contaminants (Doern, G.V. et al., "Direct Identification of *Staphylococcus aureus* in Blood Culture Fluid with a Commercial Latex Agglutination Test", J. Clin. Microbiol., Dec. 1982, pp. 1048–1051). For this reason, early identification of *S. epidermidis* may prevent unnecessary antibiotic therapy, while the identification of bacteremias caused by *S. aureus* and *St. pneumoniae* require prompt and appropriate antibiotic therapy. They account for 50% of community-acquired bacteremias in AIDS patients, and rapid diagnosis can optimize therapy (Davis, T.E. et al., "Rapid, Direct Identification of *Staphylococcus aureus* and *Streptococcus pneumoniae* from Blood Cultures Using Commercial Immunologic Kits and Modified Conventional Tests", Diagn. Microbiol. Infect. Dis. 1992, No. 15, pp. 295–300).

All known methods that are used to identify bacteria from blood cultures require either removal of liquid from the culture bottle (McDonald, C.L. et al., "Rapid Identification of *Staphylococcus aureus* from Blood Culture Bottles by a Classic 2-Hour Tube Coagulase Test", J. Clin. Microbiol., Jan. 1995, pp. 50–52) or require removal and subsequent centrifugation of liquid (Rappaport, T. et al., "Evaluation of Several Commercial Biochemical and Immunologic Methods for Rapid Identification of Gram-Positive Cocci Directly from Blood Cultures", J. Clin. Microbiol., July 1988, pp. 1335–1338).

Handling of potentially infectious liquid from culture bottles by lab personnel represents an immense hazard. Therefore, extremely careful operation by lab personnel is required, which can be very time consuming and expensive. Consequently, there exists a need for an identification method that would not require removal of hazardous liquid from blood culture bottles or from tuberculosis test vials.

As discussed above, the concept of disposing a fluorescent chemical sensor material into each blood culture bottle has been previously disclosed. This technique allows for the ability to monitor not only the production of carbon dioxide, but also the consumption of oxygen by microorganisms over time. In this way, characteristic metabolic signatures are generated that could provide a means for organism identification.

However, there is a limitation to this technique in that carbon dioxide production and oxygen consumption are very general features that apply to many microorganisms species. Theoretically, the number of fluorescent chemical sensors within each blood culture bottle could be increased in order to monitor more features. However, this appears to be rather impractical because most fluorescent sensors work at optimum in almost identical spectral regions. Therefore, their signals would highly overlap.

Consequently, there still exists a need for an identification method that would not require removal of hazardous liquid from blood culture bottles or from tuberculosis test vials, and that monitors a larger number of microorganism-specific features.

SUMMARY OF THE INVENTION

It is an objective of the present invention to overcome the above problems of the prior art by providing a method for identifying microorganisms in culture bottles that does not require removal of liquid from culture bottles, and that monitors a larger number of microorganism-specific features than has previously been monitored in known methodologies.

According to the present invention, the above objective is achieved by repetitively extracting head space gas from "positive" culture bottles, by guiding the extracted gas to a large number of non-specific gas sensors, where each of the non-specific gas sensors is sensitive to a different group of chemical compounds that are in part emitted by the growth media and in part produced by the organisms, by combining the output signals of all non-specific sensors into one multi-dimensional vector, by analyzing the features of this vector over time during the repetitive gas extraction process, and comparing the resulting feature set with previously generated feature sets of known microorganisms in order to achieve identification of the microorganisms.

DETAILED DESCRIPTION OF THE INVENTION

According to the present invention, head space gas is extracted from culture bottles that have registered positive for microorganisms on common manual or automated culture systems. Such bottles contain a standard amount of specimen such as blood and a growth medium, and contain a certain amount of head space gas. The bottles are sealed with a rubber septum, which not only allows for injection and extraction of liquid sample, but also for injection and extraction of head space gas.

In an apparatus according to the present invention, the extracted head space gas is guided to a large number of non-specific gas sensors. Each of the non-specific gas sensors is sensitive to a different group of chemical compounds that are in part emitted by the growth media and in part produced by the microorganisms. Common growth media contain a large number of ingredients such as soybean-casein, yeast, dextrose, sucrose, fructose, arginine, hemin, menadione, Vitamin $B_6$ and others. Therefore, the head space gas room is filled with a large number of volatile compounds.

If a culture bottle contains microorganisms, the microorganisms will consume volatile compounds in the liquid. As a result, the concentration of the volatile compounds in the head space will change over time, and the degree of change per compound will depend on the microorganism species. In addition, the microorganisms are producing new compounds that will end up in part in the head space gas. Again, the specific mixture of these new compounds will vary from one organism species to the next.

Figure 1:
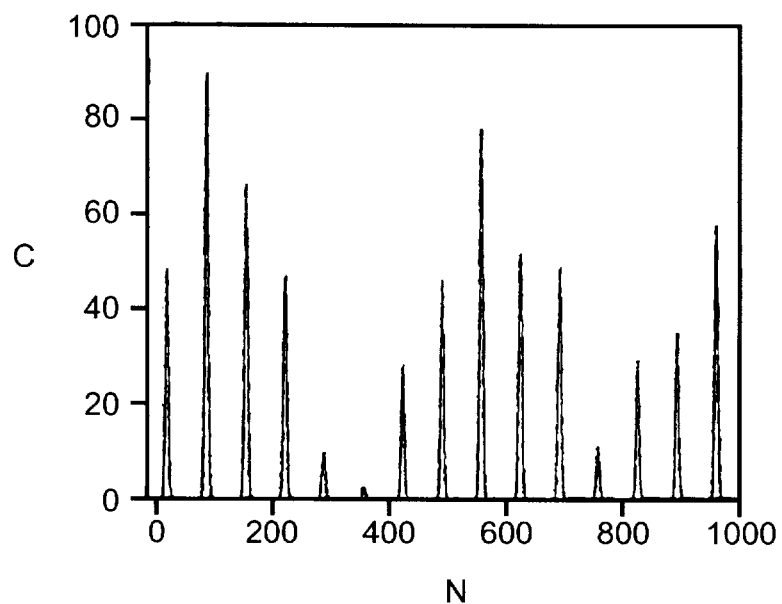
FIG. 1 depicts for a first microorganism the concentration, C, of a plurality of compounds in the head space gas of a positive culture bottle versus a parameter, N, that is different for each compound.
Figure 2:
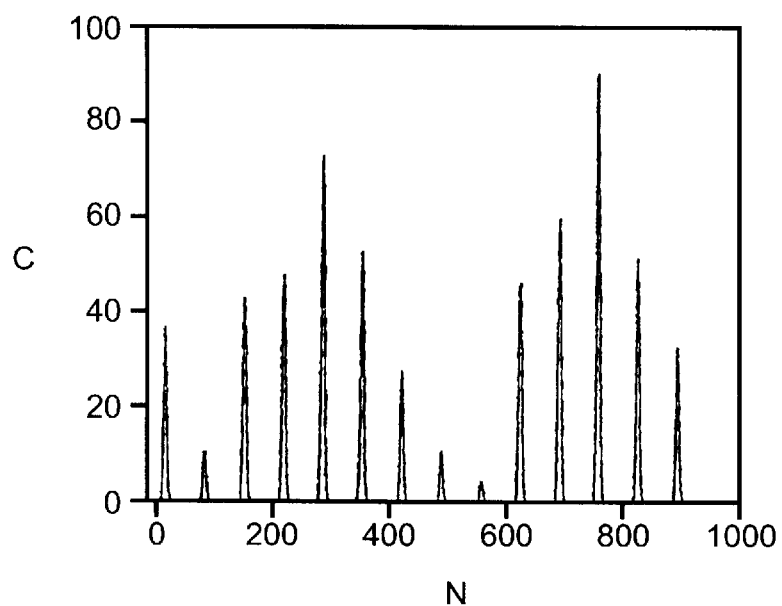
FIG. 2 depicts for a second microorganism the concentration, C, of a plurality of compounds in the head space gas of a positive culture bottle versus a parameter, N, that is different for each compound.

FIG. 1 depicts, for a first microorganism species, the concentration, C, of a plurality of compounds in the head space gas of a positive culture bottle versus a parameter, N, that is different for each compound. The quantity N could be, e.g., the molecule size of the volatile compounds. FIG. 2 depicts, for a second microorganism species, the concentration, C, of a plurality of compounds in the head space gas of a positive culture bottle versus N. The distribution C(N) is different for the two microorganism species, because every organism has its very specific metabolic activity pattern.

Figure 3:
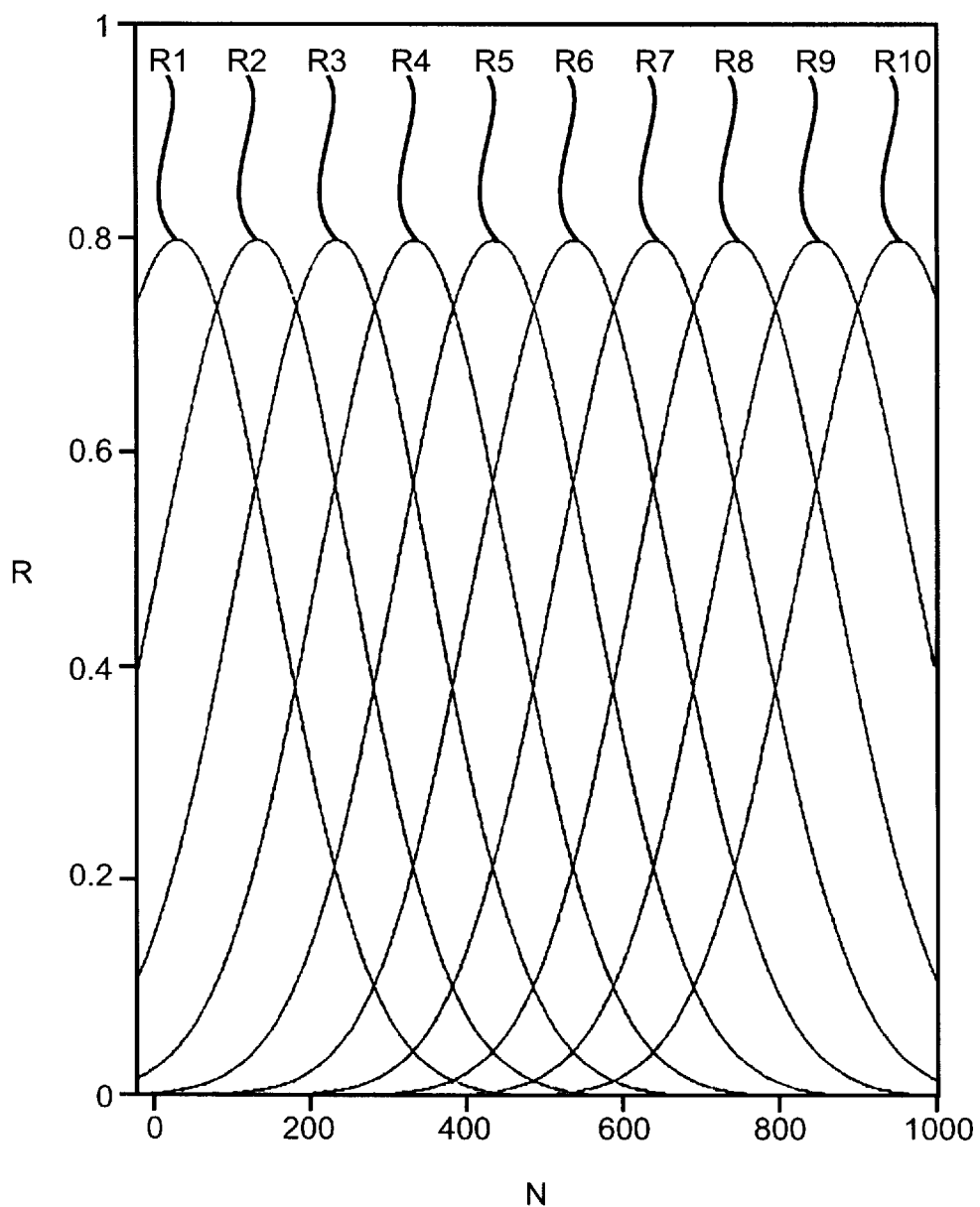
FIG. 3 shows the response curves, R1, R2, R3,...R10 of ten non-specific sensors versus a parameter, N, that is different for each compound.

FIG. 3 shows the response curves, R1, R2, R3,...R10 of ten non-specific sensors versus the parameter N. Each sensor is responding to a whole group of compounds. The response curves are bell-shaped, and the location of the bells along the N axis varies from one sensor to the next.

Figure 4:
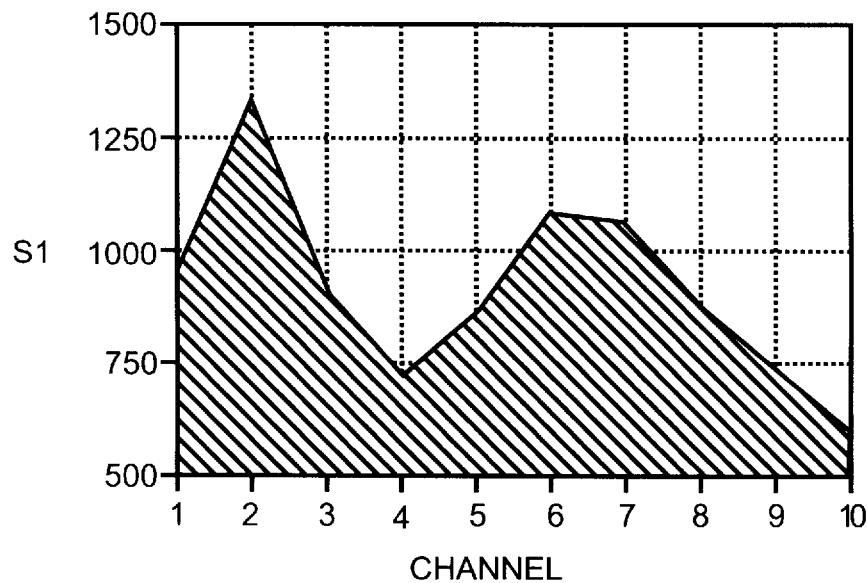
FIG. 4 illustrates the output signals, S1, of all ten non-specific sensors in response to the first microorganism shown in FIG. 1. The ten output signals form a ten-dimensional vector, which is, for illustration purposes, shown as an area graph.

By combining the distribution of compounds, C(N) in FIG. 1, with the response curves, R(N) in FIG. 3, one obtains an output signal, S1, for each of the ten sensor channels. The output signal of each channel is the result of the sensor's response to a whole group of components. How many components contribute to the output signal depends on the width of the bell-shaped response curve of the particular sensor. FIG. 4 depicts the ten channel signals that are obtained for the first microorganism. In general, these ten signals represent the components of a ten-dimensional vector. For the purpose of illustration, this vector is shown in FIG. 4 as an area graph.

Figure 5:
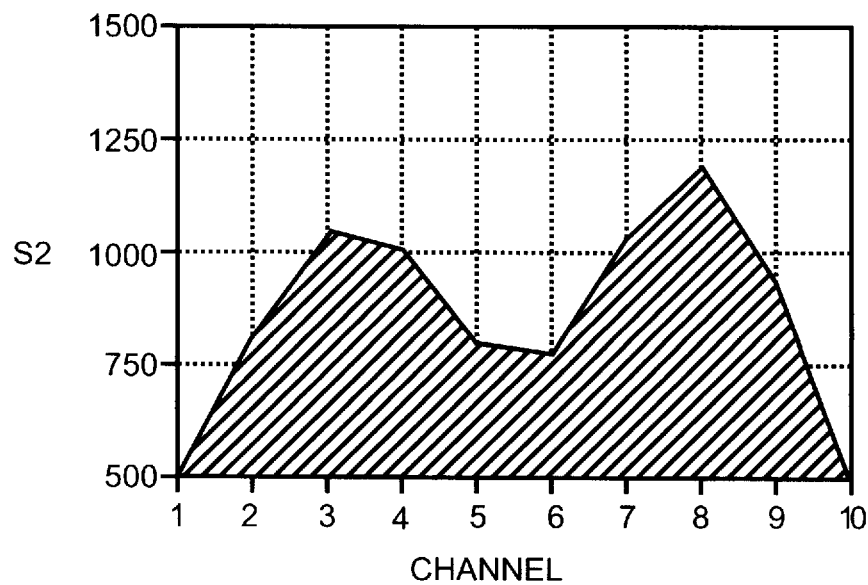
FIG. 5 illustrates the output signals S2, of all ten non-specific sensors in response to the second microorganism shown in FIG. 2. The ten output signals form a ten-dimensional vector, which is, for illustration purposes, shown as an area graph.

If the same procedure is being applied to the distribution C(N) of the second microorganism species, shown in FIG. 2, the area graph of FIG. 5 is obtained. A comparison of FIGS. 4 and 5 indicates pronounced differences in the two graph profiles. In other words, the two ten-dimensional vectors have different feature sets. By analyzing the features of these vectors over time during a repetitive gas extraction process, and by comparing the resulting feature sets with previously generated feature sets of known microorganisms, an identification of unknown organisms can be achieved.

An apparatus according to the present invention is not limited to ten sensors (i.e. FIG. 3). In general, the identification capability will increase with the number of sensors. In a preferred embodiment, the number of sensors can be from 10 to 30sensors. An apparatus according the present invention does not need to detect compounds that are produced by the microorganisms. Even if no volatile compound would be produced by the microorganisms, the consumption of compounds that are present in the growth media would allow for microorganism identification. Growth media are produced under very controlled conditions to allow for optimum microorganism detection. Therefore, the concentration distribution of volatile compounds in the head space will be very repeatable. Due to organism metabolism, this distribution is changed. It is advantageous, however, that, in addition to their consumption, microorganisms are producing certain new compounds. This second effect results in an increased identification capability.

The procedure of generating multi-dimensional vectors, analyzing their features, and comparing the resulting feature sets with previously generated feature sets of known microorganisms can be accomplished by utilizing various available software programs known to anyone of ordinary skill in the art.

Furthermore, monitoring the consumption of volatile compounds that are emitted constantly by the growth media and/or monitoring the production of new volatile compounds produced by the microorganisms can be achieved by using many different types of non-specific gas sensors. Thus, for example, in a preferred embodiment, sensor arrays (i.e, an array of gas sensors) based on piezo-resonators can be utilized. In these sensor arrays, each element has a differently treated surface, so that different compounds adhere to different elements. Loading a surface with molecules of these compounds results in a change of the element's resonance frequency. The change in frequency is a measure of the amount of molecules that have settled on the surface, and the number of molecules is related to the density of those molecules within the head space gas.

The sensor area is currently under rapid development and it is very likely that new non-specific sensors will be developed in the future. It is intended that all such sensors are to be encompassed by the present invention.

Figure 6:
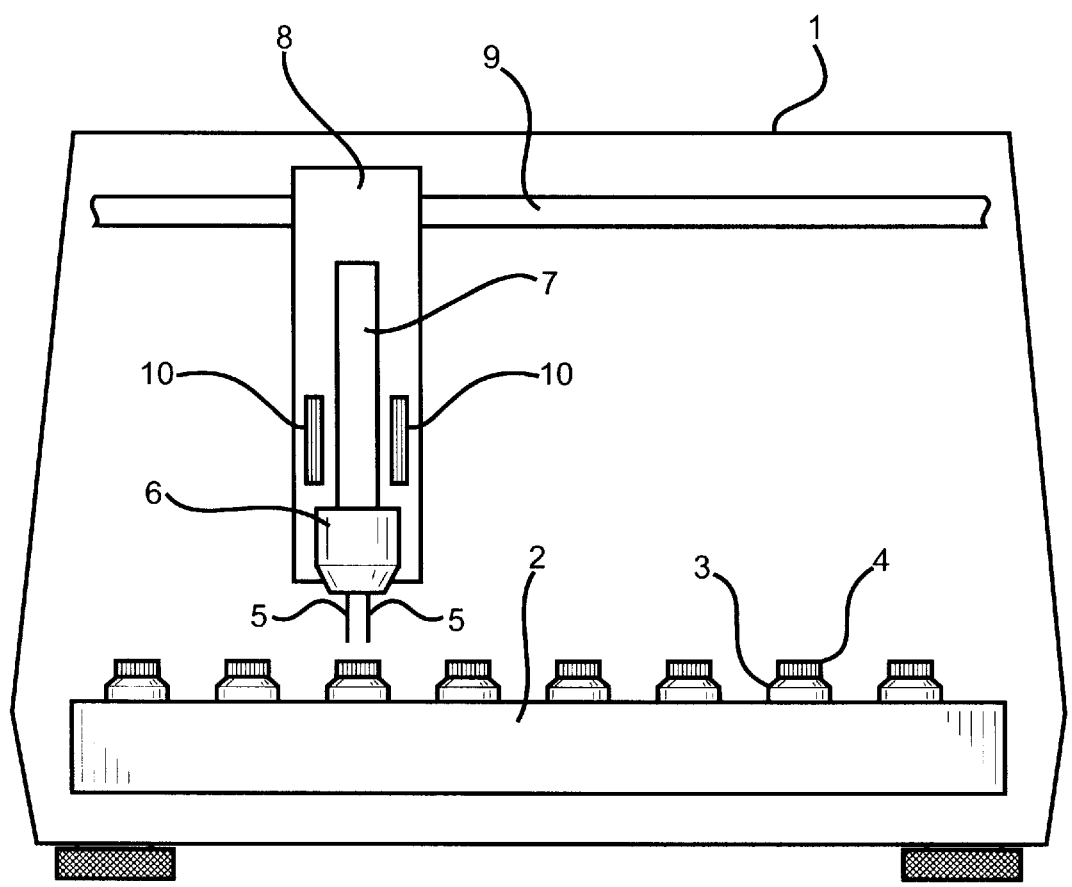
FIG. 6 shows a schematic view of a microorganism identification apparatus according to the present invention.

FIG. 6 depicts schematically a microorganism identification apparatus in accordance with the present invention. The apparatus comprises a tray 2 inside a thermally insulated instrument housing 1. A number of positive culture bottles 3 which are sealed by means of a rubber-like septum 4 are arranged in a regular pattern on tray 2. A pair of two hollow stainless steel pencil-point needles 5 is connected to a sensor head 6 comprising a plurality of non-specific gas sensors. Sensor head 6 is mounted to a first vertical rail 7 and can be moved downward and upward on a block 8. If moved downward to a first position, needles 5 will penetrate septum 4. In this first position, head space gas is extracted from the culture bottle 3, through the needle(s) 5 and into sensor head 6, where the head space gas is analyzed for the concentration of volatile compounds therein. It is possible either to circulate the head space gas through one of the needles to the sensor head and then through the other needle back to the bottle, or to extract the head space gas, and refill the head space with a culture gas using an external gas tank.

Once a bottle has been analyzed, sensor head 6 is moved upward along rail 7 into a second position. Here, a set of heaters 10 is activated to sterilize the needles and to prevent cross-contamination between different bottles. After sterilizing the needles, block 8 is moved horizontally along a second rail 9 until the needles are in a position from where they can reach another bottle. Then, sensor head 6 is moved downward, and the same procedure is repeated.

Sensor head 6 is connected with a computer, where the data is stored and analyzed. As has been mentioned above, microorganism identification is achieved by comparing the resulting feature sets with previously generated feature sets of known microorganisms that are stored already within the computer.

It should be understood that FIG. 6 demonstrates one embodiment of the present invention. In other embodiments, the apparatus of the present invention can utilize a tray capable of containing at least one culture bottle, or up to ten culture bottles or up to one hundred culture bottles. In a further embodiment, the apparatus of the present invention can be utilized to identify microorganisms in up to two hundred fifty culture bottles on trays placed in this apparatus.

Therefore, the process of microorganism identification can be rapidly accomplished, i.e., within one to three hours. Furthermore, since no liquid is removed from the culture bottles in the present invention, the danger of infection to lab personnel is greatly reduced, making the present invention a very effective means for identification of microorganisms.

We claim:

1. A method for identifying microorganisms directly in a culture bottle without removal of liquid from said culture bottle, the culture bottle having been identified as positive for microorganisms, wherein said culture bottle also contains a specimen, a growth medium and a head space gas, said method comprising:

repetitively extracting head space gas from said culture bottle;

guiding the repetitively extracted head space gas to an array of non-specific gas sensors for repetitively measuring the concentration of compounds in the head space gas over a period of time;

repetitively monitoring the consumption of volatile compounds that have been emitted by the growth media and the production of new volatile compounds that are produced by the microorganisms over the period of time and generating data representative of said monitoring; and comparing the data generated by repetitively monitoring the consumption of compounds using the array of non-specific gas sensors with previously generated data of known microorganisms so to identify an unknown microorganism in said culture bottle using a computer connected to the sensor array.

2. The method of claim 1 wherein the extracted head space gas is recirculated into the culture bottle after analyzing it at said array of sensors.

3. A method for identifying microorganisms directly in culture bottles without removal of liquid from said culture bottles, these culture bottles having become positive for microorganisms, wherein each of said culture bottles also contains a specimen, a growth medium and a head space gas, and wherein each of said bottles are sealed with a rubber septum, said method comprising:

placing said sealed culture bottles on a tray in an apparatus for repetitively extracting said head space gas;

moving a mounted sensor head having a plurality of non-specific gas sensors and two needles connected to the bottom of the sensor head downward to a first position to penetrate the septum of the culture bottle;

repetitively extracting head space gas from the culture bottle into the sensor head over a period of time for analysis of the concentration of compounds in the sealed culture bottle, wherein each of the non-specific gas sensors in the sensor head repetitively analyzes the concentration of a different group of chemical compounds that are in part emitted by growth media and in part produced by microorganisms over the period of time;

comparing the data generated by the analysis of the concentration of said compounds with previously generated data of known microorganisms using a computer connected to the sensor head so to identify an unknown microorganism in the sealed culture bottle;

moving the sensor head upward after analysis of the culture bottle to a second position;

sterilizing the needles in order to prevent cross-contamination between different bottles;

then, moving the sensor head horizontally until the needles are in a position to penetrate the septum of a second culture bottle;

moving the sensor head downward to the first position and repeating the above procedure with a second culture bottle;

repeating this method with as many culture bottles as are in the tray; and identifying unknown microorganisms within each culture bottle by comparing the data generated by the analysis of the concentration of said compounds with previously generated data of known microorganisms using a computer connected to the sensor head.

4. The method of claim 3 wherein said needles are hollow stainless steel pencil point needles.

5. The method of claim 3 wherein each of said non-specific gas sensors is sensitive to a different group of chemical compounds that are in part emitted by growth media and in part produced by microorganisms.

6. The method of claim 3 wherein the head space gas is circulated through one of the needles to the sensor head and then through the other needle back to the bottle.

7. The method of claim 3 wherein the head space gas is extracted from the sealed culture bottle and the head space is refilled with a culture gas using an external gas tank.

8. The method of claim 3 wherein said needles are sterilized by a set of heaters in the apparatus.

* * * * *